United States Patent [19]

Asgharian et al.

[11] Patent Number: 5,494,937
[45] Date of Patent: Feb. 27, 1996

[54] SALINE SOLUTION FOR TREATING CONTACT LENSES

[75] Inventors: Bahram Asgharian; Masood Chowhan, both of Arlington, Tex.; Paul Stach, Upper Arlington, Ohio

[73] Assignee: Alcon Laboratories, Inc., Fort Worth, Tex.

[21] Appl. No.: 278,767

[22] Filed: Jul. 22, 1994

[51] Int. Cl.$^6$ ..................................................... A61K 9/00
[52] U.S. Cl. ...................... 514/772.3; 514/839; 514/912; 514/915; 252/174.21; 252/106; 252/173
[58] Field of Search ................................ 514/772.3, 839, 514/912, 915; 424/429

[56] References Cited

U.S. PATENT DOCUMENTS

| | | | |
|---|---|---|---|
| 4,053,628 | 11/1977 | Stevenson et al. | 424/283 |
| 4,312,833 | 1/1982 | Clough et al. | 252/188.3 |
| 4,525,346 | 6/1985 | Stark | 424/80 |
| 4,568,517 | 2/1986 | Kaspar et al. | 252/188.2 |
| 4,710,313 | 12/1987 | Miyajima et al. | 252/105 |
| 4,758,595 | 7/1988 | Ogunbiyi et al. | 514/635 |
| 4,808,239 | 2/1989 | Schafer et al. | 134/42 |
| 4,820,352 | 4/1989 | Riedhammer et al. | 514/839 |
| 5,011,661 | 4/1991 | Schäfer et al. | 514/840 |

FOREIGN PATENT DOCUMENTS

93/21903  11/1993  WIPO.

OTHER PUBLICATIONS

Collin, et al., "The Effects of Na$_2$EDTA on Keratocytes and Endothelium of Isolated Guinea Pig Cornea", *International Contact Lens Clinic*, vol. 9, No. 5, pp. 281–287 (Sep./Oct. 1982).

"Guide to ICI Surfactants", *ICI Specialty Chemicals*.

"R.I.T.A. Pationic Acyl Lactyaltes and Patlac Lactic Salts", R.I.T.A. Corporation, Woodstock, IL, pp. 1–57.

"ALLERGAN® HYDROCARE® Preserved Saline Solution", 1993 *Physicians' Desk Reference For Ophthalmology*, 21st Edition, C. Weisbecker, et al., Editorial Consultants, Medical Economics Data, Montvale, NJ, pp. 336–338.

"Bausch & Lomb ReNu® Saline Solution", 1990 *Physicians' Desk Reference For Ophthalmology*, 18th Edition, J. Walsh, et al., Editorial Consultants, Medical Economics Company Inc., Oradell, NJ, pp. 244–247.

*Primary Examiner*—Thurman K. Page
*Assistant Examiner*—Pamela S. Webber
*Attorney, Agent, or Firm*—James A. Arno; Gregg C. Brown

[57] ABSTRACT

Saline solutions useful in treating contact lenses are described. Unlike prior saline solutions used for similar purposes, the present solutions do not contain conventional antimicrobial agents which are potentially toxic to ocular tissues. Rather, the solutions contain a combination of a borate-polyol complex, one or more anionic or nonionic surfactants, and a low molecular weight amino acid (e.g., glycine). It has been found that this combination effectively preserves the saline solutions from antimicrobial contamination, is relatively nontoxic to ocular tissues, and is compatible with oxidizing agents used in certain contact lens disinfecting systems. The combination also facilitates the cleaning of contact lenses.

13 Claims, No Drawings

SALINE SOLUTION FOR TREATING CONTACT LENSES

BACKGROUND OF THE INVENTION

The present invention relates to the field of products for treating contact lenses. More specifically, the invention relates to improved saline solutions for rinsing, soaking and storing contact lenses. The saline solutions of the present invention are believed to represent a significant improvement over prior saline solutions utilized for similar purposes, because the present solutions do not contain conventional antimicrobial preservatives which have been frequently associated with various toxic effects on ophthalmic tissues. Prior saline solutions have been either preserved or unpreserved. The antimicrobial agents utilized in the preserved salines have principally been sorbic acid or thimerosal, although polymeric antimicrobial agents have also been utilized. Salines which are preserved with sorbic acid or thimerosal are known to discolor lenses, and thimerosal is known to cause hypersensitivity reactions in some patients. These prior saline solutions are also incompatible with oxidizing agents, such as chlorine, hypochlorous acid and iodine.

Ethylenediaminetetraacetic acid and the monosodium, disodium and trisodium salts thereof (collectively referred to herein as "EDTA") have been widely used for many years in ophthalmic products, particularly products for treating contact lenses, such as saline solutions. EDTA has been utilized in preserved saline solutions to enhance the antimicrobial efficacy of the above-mentioned chemical preservatives, particularly the efficacy of those preservatives against gram negative bacteria. However, some scientific studies have indicated that EDTA may damage corneal cells. See, e.g., Collin, et al., "The Effects of $Na_2EDTA$ on Keratocytes and Endothelium of the Isolated Guinea Pig Cornea", *International Contact Lens Clinic*, volume 9, number 5, September/October 1982. Further, it is also incompatible with certain components of compositions for treating contact lenses, such as chlorine, iodine and other oxidizing agents.

Unpreserved saline solutions marketed in multi-dose containers are either packaged in aerosol containers or squeezable plastic bottles. Saline solutions packaged in aerosol cans are expensive due to the cost of containers and specialized technology. Moreover, saline solutions contained in aerosol cans are Gamma irradiated to achieve sterility; this produces peroxides in the solutions. These peroxides react with chlorine or hypochlorous acid to form microbiologically inactive chloride. Consequently, aerosol salines are not compatible with contact lens disinfecting systems which use oxidizing agents such as chlorine, hypochlorous acid or iodine. Unpreserved salines may also be packaged in squeezable bottles; however, these solutions have poor antimicrobial activity and must be discarded after 30 days of use once the container is opened.

In 1990, a second generation saline solution which eliminated some of the disadvantages of the first generation saline solutions was introduced. However, this saline solution, which contains fifty pans per million of metaborate as a preservative, may cause corneat damage upon long-term use. Moreover, peroxide-preserved saline solutions are not compatible with oxidizing agents like chlorine. This incompatibility precludes the use of peroxide-preserved saline solutions as diluents for contact lens disinfecting tablets containing chlorine or other oxidizing agents.

In view of the foregoing circumstances, there is a need for improved saline solutions for treating contact lenses which are: (1) adequately preserved to prevent any risk of antimicrobial contamination of the solution or contact lenses treated with the solution, (2) nontoxic to ophthalmic tissues and (3) chemically compatible with oxidizing agents. There is particularly a need for a preserved, multidose saline solution which meets the foregoing requirements and does not contain EDTA. The present invention is directed to satisfying these needs.

SUMMARY OF THE INVENTION

The present invention is based on the finding that a combination of a borate-polyol complex, an anionic and/or nonionic surfactant, and a low molecular weight amino acid (e.g., glycine) provides a saline solution which has adequate antimicrobial activity so as to be preserved against contamination by bacteria and other microorganisms, but is relatively nontoxic to ophthalmic tissues, particularly the cornea. This saline solution is also chemically compatible with oxidizing agents, such as chlorine, used in certain contact lens disinfection systems. In addition to the above-cited advantages, the improved saline solutions of the present invention also facilitate the cleaning of contact lenses.

The present invention is based, in part, on a new use of glycine and other low molecular weight amino acids. The present inventors have found that such amino acids enhance the activity of antimicrobial preservatives, and are also useful as chelating agents. The low molecular weight amino acids can also serve as buffers and tonicity agents.

The self-preserved saline solutions of the present invention can be utilized to treat all known types of contact lenses. The solutions can be used for various purposes, such as thermal disinfection of the lenses when used in conjunction with a heating unit, as well as daily cleaning, rinsing and storage of contact lenses. Further, the solutions are particularly useful solvents for disinfecting tablets or other solid disinfecting agents, particularly tablets which contain an oxidizing agent such as chlorine, hypochlorous acid, or iodine. The solutions may also be utilized as solvents for solid cleaning agents, such as tablets containing one or more protcolytic enzymes.

The saline solutions of the present invention may be used for thirty days or more once the container is opened. Unlike prior saline solutions containing sorbic acid or thimerosal, the solutions of the present invention do not discolor contact lenses. Also, the saline solutions of the present invention preferably do not contain EDTA; the absence of EDTA in the solutions eliminates the risk of damage to corneal cells. Finally, the cost of the solutions of the present invention is significantly less than that of the prior aerosol saline solutions.

DESCRIPTION OF PREFERRED EMBODIMENTS

The improved saline solutions of the present invention contain a borate-polyol complex. As used herein, the term "borate" shall refer to boric acid, salts of boric acid and other pharmaceutically acceptable borates, or combinations thereof. Most suitable are: boric acid, sodium borate, potassium borate, calcium borate, magnesium borate, manganese borate, and other such borate salts. As used herein, and unless otherwise indicated, the term "polyol" shall refer to any compound having at least two adjacent —OH groups which are not in trans configuration relative to each other.

The polyols can be linear or circular, substituted or unsubstituted, or mixtures thereof, so long as the resultant complex is water-soluble and pharmaceutically acceptable. Such compounds include sugars, sugar alcohols, sugar acids and uronic acids. Preferred polyols are sugars, sugar alcohols and sugar acids, including, but not limited to: mannitol, glycerin, propylene glycol and sorbitol. Especially preferred polyols are mannitol and glycerin; most preferred is mannitol. The use of borate-polyol complexes in ophthalmic compositions is described in copending, commonly assigned U.S. patent application Ser. No. 08/198,427 filed Feb. 21, 1994, and in corresponding PCT International Application Number PCT/US93/04226 (International Publication Number WO 93/21903); the entire contents of the foregoing applications are hereby incorporated in the present specification by reference.

The water-soluble borate-polyol complexes utilized in the present invention may be formed by mixing borate with the polyol(s) of choice in an aqueous solution. The molar ratio of borate to polyol is generally between about 1:0.1 and about 1:2, and is especially between about 1:0.25 and about 1:0.75. Some borate-polyol complexes, such as potassium borotartrate, are commercially available.

The borate-polyol complexes are utilized in the saline solutions of the present invention in an amount of from about 0.5 to about 6.0 percent by weight/volume "w/v %", preferably from about 1.0 to about 2.5 w/v %.

The saline solutions of the present invention also contain one or more anionic or nonionic surfactants which are surface active and have at least some limited antimicrobial activity. More specifically, the surfactants must be surface active, so as to promote the removal of deposits from contact lenses, and must have the ability to kill and/or prevent the proliferation of microorganisms commonly found on contact lenses, particularly gram-positive bacteria such as *Staph. aureus*. The surfactants must also have a low incidence of ocular irritation.

The preferred suffactants are anionic. More specifically, the preferred surfactants have alkyl or alkylethoxylate backbones and include anionic groups, such as carboxylic, lactic, succinic or glutamic groups. Alkyl ethoxylates are particularly preferred. The surfactants will typically contain $C_8$ to $C_{18}$ alkyl chains and from 1 to 20 polyethylene oxide groups.

The most preferred anionic suffactants are the acyl lactylate surfactants which are commercially available under the name "Pationic™" from R. I. T. A. Corporation, located in Woodstock, Ill. (USA), and have the following formula:

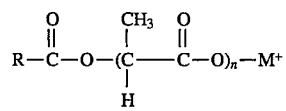

wherein R is $C_{10}$ to $C_{30}$ alkyl, n is 1, 2 or 3, and M is a monovalent cation, such as sodium or potassium. The most preferred of these surfactants is sodium lauroyl lactylate, which is sold under the name "Pationic™ 138C" and has the following formula:

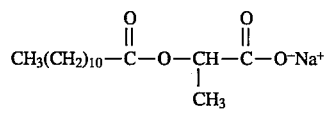

In addition to being surface active agents, these anionic surfactants also have antimicrobial activity, particularly against gram-positive organisms such as *Staph. aureus*.

The nonionic surfactants which may be utilized in the present invention include alkyl ethoxylates, alkyl phenyl ethoxylates, and ethylene oxidd propylene oxide block copolymers. The preferred nonionic suffactants are polyoxyethylene lauryl ethers, such as polyoxyethylene (23) lauryl ether, which is commercially available from ICI Speciality Chemicals, Wilmington, Dela. (USA), under the tradename "Brij® 35".

The saline solutions of the present invention may contain combinations of two or more surfactants, including combinations of anionic and nonionic surfactants. The total amount of surfactant utilized will generally be in the range of from about 0.001 to about 0.1 w/v %, preferably from about 0.005 to about 0.05 w/v %.

The amino acids which may be utilized in the present invention have a molecular weight in the range of 75 to 250. The following compounds are representative of the low molecular weight amino acids which may be utilized in the present invention:

| | |
|---|---|
| L - Alanine | Glycine |
| β - Alanine | Histidine |
| α - Aminoadipic Acid | Cystine |
| α - Aminobutyric Acid | Leucine |
| γ - Aminobutyric Acid | Lysine |
| α - Aminoisobutyric Acid | Norleucine |
| Arginine | Ornithine |
| Asparagine | Phenylalanine |
| Aspartic Acid | Phophoserine |
| Citrulline | Sarcosine |
| Creatine | Threonine |
| Glutamic Acid | Valine |

Amino acids which include alpha (α) carboxylic acid groups are preferred.

The amount of amino acid utilized will depend on the molecular weight of the amino acid(s) selected. In general, one or more of the above-described amino acids will be utilized in a concentration of from about 0.1 to about 7.5 w/v %.

The most preferred amino acid for use in the present invention is glycine. Glycine is a relatively simple, low molecular weight amino acid. It is also known as "aminoacetic acid". The amount of glycine utilized in the compositions of the present invention will vary depending on the type of composition in which it is contained, and the function of glycine in the composition. In general, compositions which contain glycine for purposes of enhancing the activity of an antimicrobial preservative contained therein will contain glycine in an amount of from about 0.1 to about 2.5 w/v %, preferably from about 0.1 to about 1.0 w/v %. Similar amounts of glycine will be utilized to perform the other functions mentioned above.

The above-described saline solutions may be used to treat contact lenses in accordance with processes known to those skilled in the art. For example, the solutions can be utilized to clean a contact lens by first removing the lens from the eye of the patient, placing a few drops of the solution on the lens, and rubbing the solution over the surfaces of the lens while in the palm of the hand. The saline solutions can also be utilized in more passive cleaning processes, wherein the solutions are merely used to rinse debris from contact lenses. And, the solutions can be utilized as diluents for enzymatic cleaning tablets. The solutions can also be used in connection with the disinfection of contact lenses. More specifically, the saline solutions may be utilized as solvents for contact lens disinfecting tablets; the lenses are soaked in the resulting solution for sufficient time to disinfect and neutralize. Alternatively, contact lenses can be heat sterilized using thermal disinfecting units filled with the above-described saline solutions. Since the saline solutions of the present invention are self preserved, the risk of microbial contamination when the lenses are stored following disinfection is minimized.

The following examples are presented to further illustrate the improved saline solutions of the present invention.

EXAMPLE 1

| Ingredient | Concentration (w/v %) |
|---|---|
| Boric Acid | 1.0 |
| Mannitol | 1.5 |
| Glycine | 0.75 |
| Pationic 138C | 0.01 |
| KOH/HCl | pH7.4 |
| Purified Water | q.s. |

The above composition may be prepared by sequentially adding the ingredients to a portion of the distilled water and stirring the solution until each of the ingredients has dissolved. When all of the ingredients have been dissolved, the solution is brought to final volume by the addition of the remainder of the water, and the pH is adjusted, if necessary. The solution has an osmolality of 295 mOsm/Kg. It has been tested and found to meet the United States Pharmacopeia ("USP") and United States Food and Drug Administration ("FDA") requirements for preservative effectiveness; those requirements are referred to below by means of the term "PET", which is an abbreviation of "preservative effectiveness test". The above-described composition is referred to below as "Formulation A".

EXAMPLE 2

The antimicrobial efficacy of Formulation A was evaluated. More specifically, the antimicrobial activity this saline solution was evaluated by inoculating 20 milliliters ("ml") of the solution with 0.1 ml of a microbial suspension. The final concentration was approximately $10^6$ colony forming units per ml. At each time pull, the number of survivors was determined by taking a 1 ml aliquot of the test sample, serially diluting in 9 ml of saline at selected time intervals and preparing pour plates of SCDA. The bacteria and yeast plates were incubated at 30° C. to 35° C. for two to three days. The mold plates were incubated at 20° to 25° C. for five days. The results are presented in Table 1 below.

TABLE 1

Antimicrobial Activity of Formulation A Against PET Microorganisms

| Organism | Time | Log Reduction |
|---|---|---|
| A. niger | 7 Days | 2.5 |
| | 14 Days | 1.5 |
| | 21 Days | 1.5 |
| | 28 Days | 1.4 |
| | 35 Days | 1.6 |
| C. albicans | 7 days | 3.7 |
| | 14 Days | 4.7 |
| | 21 Days | 3.2 |
| | 28 Days | 4.5 |
| P. aeruginosa | 7 Days | 3.5 |
| | 14 Days | 5.2 |
| | 21 Days | 3.1 |
| | 28 Days | 3.8 |
| E. coli | 7 Days | 3.5 |
| | 14 Days | 4.9 |

TABLE 1-continued

Antimicrobial Activity of Formulation A Against PET Microorganisms

| Organism | Time | Log Reduction |
|---|---|---|
| | 21 Days | 3.3 |
| | 28 Days | 3.9 |
| S. aureus | 7 Days | 5.0 |
| | 14 Days | 5.0 |
| | 21 Days | 4.9 |
| | 28 Days | 4.6 |

EXAMPLE 3

| Ingredient | Concentration (w/v %) |
|---|---|
| Boric Acid | 1.0 |
| Mannitol | 1.5 |
| Glycine | 0.75 |
| Pationic 138C | 0.01 |
| Brij 35 | 0.01 |
| KOH/HCl | pH7.4 |
| Purified Water | q.s. |

The above composition represents another example of the improved saline solutions of the present invention. The formula of this composition is the same as that of Formulation A (see Example 1 above), except for the inclusion of a nonionic surfactant (i.e., Brij 35). This composition, which is referred to herein as "Formulation B", may be prepared in accordance with the procedure described in Example 1. A summary of the activity of Formulation B against the PET microorganisms is presented in Table 2 below.

TABLE 2

Antimicrobial Activity of Formulation B Against PET Microorganisms

| Organism | Time | Log Reduction |
|---|---|---|
| A. niger | 6 Hrs. | 1.0 |
| | 24 Hrs. | 1.7 |
| | 7 Days | 4.4 |
| | 14 Days | 4.3 |
| | 28 Days | 4.5 |
| C. albicans | 6 Hrs. | 1.2 |
| | 24 Hrs. | 1.9 |
| | 7 Days | 5.0 |
| | 14 Days | 5.0 |
| | 28 Days | 5.0 |
| E. coli | 6 Hrs. | ND |
| | 24 Hrs. | ND |
| | 7 Days | 5.9 |
| | 14 Days | 5.9 |
| | 28 Days | 5.9 |
| P. aeruginosa | 6 Hrs. | 0.9 |
| | 24 Hrs. | 1.4 |
| | 7 Days | 4.8 |
| | 14 Days | 5.7 |
| | 28 Days | 6.4 |
| S. aureus | 6 Hrs. | 0.4 |
| | 24 Hrs. | 1.5 |
| | 7 Days | 4.8 |
| | 14 Days | 5.5 |
| | 28 Days | 6.5 |

ND = Not Determined

EXAMPLE 4

The following compositions were tested to determine if EDTA could simply be eliminated from saline solutions; the compositions were prepared by means of procedures similar to the procedure described in Example 1 above:

| Ingredient | Concentration (w/v %) | | |
|---|---|---|---|
| | Formulation C | Formulation D | Formulation E |
| Boric Acid | 0.442 | 0.442 | 0.442 |
| Sodium Borate | 0.0875 | 0.0875 | 0.0874 |
| Sodium Chloride | 0.675 | 0.675 | 0.675 |
| Pationic 138C | — | 0.01 | 0.01 |
| Disodium Edetate | — | — | 0.1 |
| Purified Water | q.s | q.s. | q.s. |

Formulation C has a pH of 7.7 and osmolality of 299 mOsm/kg, Formulation D has a pH of 7.7 and osmolality of 294 mOsm/kg, and Formulation E has a pH of 7.3 and osmolality of 305 mOsm/kg. The compositions were tested for antimicrobial activity by means of the procedures described in Example 2. The results, expressed as the number of log reductions after 7 days, are listed below:

| Antimicrobial Activity (i.e., Log Reduction at Day 7) Against PET Microorganisms | | | |
|---|---|---|---|
| | Formulation C | Formulation D | Formulation E |
| A. niger | 1.8 | 1.9 | 1.0 |
| P. aeruginosa | 0.0 | 0.4 | 4.1 |
| S. aureus | 1.6 | 4.1 | 5.0 |

Both Formulation C and Formulation D failed the USP and FDA requirements for preservative efficacy, while Formulation E met those requirements. These results clearly demonstrate that EDTA cannot simply be eliminated. This is particularly true relative to *Pseudomonas aeruginosa*. However, the results presented in Examples 2 and 3 above demonstrate that EDTA can be replaced by low molecular weight amino acids, such as glycine.

What is claimed is:

1. A saline solution useful in the treatment of contact lenses, said solution comprising water and a single preservative system to prevent microbial contamination of the solution, said preservative system consisting of:

0.5 to 6.0 w/v % of a borate-polyol complex wherein the molar ratio of borate to polyol is from 1:0.1 to 1:1;

0.001 to 0.1 w/v % of a surfactant having antimicrobial activity; and 0.1 to 7.5 w/v % of a low molecular weight amino acid; wherein EDTA is absent from the solution.

2. A saline solution according to claim 1, wherein the low molecular weight amino acid has a molecular weight in the range of 75 to 250.

3. A saline solution according to claim 2, wherein the low molecular weight amino acid includes an alpha carboxylic acid group.

4. A saline solution according to claim 2, wherein the low molecular weight amino acid comprises glycine.

5. A saline solution according to claim 4, wherein the borate-polyol complex comprises borate and mannitol.

6. A saline solution according to claim 1, wherein the surfactant comprises an anionic surfactant.

7. A saline solution according to claim 6, wherein the anionic surfactant comprises an alkyl ethoxylate having at least one carboxylic functional group.

8. A saline solution according to claim 6, wherein the anionic surfactant comprises a surfactant having the following formula:

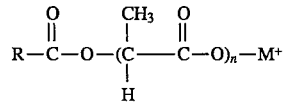

wherein R is $C_{10}$ to $C_{30}$ alkyl, n is 1, 2 or 3, and M is a monovalent cation.

9. A saline solution according to claim 8, wherein the anionic surfactant comprises sodium lauroyl lactylate.

10. A saline solution according to claim 1, wherein the surfactant comprises a nonionic surfactant.

11. A saline solution according to claim 10, wherein the nonionic surfactant is selected from the group consisting of alkylethoxylates, alkylphenyl ethoxylates and ethylene oxide/propylene oxide block copolymers.

12. A saline solution according to claim 10, wherein the nonionic surfactant comprises a polyoxyethylene lauryl ether surfactant.

13. A saline solution according to claim 1, wherein the surfactant comprises a combination of a nonionic surfactant and an anionic surfactant.

* * * * *